(12) United States Patent
Heinonen

(10) Patent No.: US 6,951,216 B2
(45) Date of Patent: Oct. 4, 2005

(54) APPARATUS AND METHOD FOR USE IN NON-INVASIVELY DETERMINING CONDITIONS IN THE CIRCULATORY SYSTEM OF A SUBJECT

(75) Inventor: Erkki Heinonen, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 138 days.

(21) Appl. No.: 10/325,534

(22) Filed: Dec. 19, 2002

(65) Prior Publication Data

US 2004/0118402 A1 Jun. 24, 2004

(51) Int. Cl.$^7$ .............................................. A61M 16/00
(52) U.S. Cl. .............................. 128/203.25; 128/205.12
(58) Field of Search .................... 128/201.13, 203.16, 128/203.17, 203.26, 204.17, 205.12, 914, 203.25

(56) References Cited

U.S. PATENT DOCUMENTS

| | | | | | |
|---|---|---|---|---|---|
| 4,112,938 | A | * | 9/1978 | Jeretin ..................... | 128/204.23 |
| 4,233,842 | A | * | 11/1980 | Raemer et al. ........... | 73/861.04 |
| 4,318,398 | A | * | 3/1982 | Oetjen et al. ............ | 128/201.13 |
| 4,326,513 | A | * | 4/1982 | Schulz et al. ........... | 128/203.14 |
| 4,327,717 | A | * | 5/1982 | Oetjen et al. ............ | 128/201.13 |
| 4,537,190 | A | * | 8/1985 | Caillot et al. ............ | 128/204.22 |
| 4,608,995 | A | * | 9/1986 | Linnarsson et al. ......... | 600/526 |
| 4,637,385 | A | * | 1/1987 | Rusz ..................... | 128/204.21 |
| 5,255,674 | A | * | 10/1993 | Oftedal et al. ......... | 128/203.16 |
| 5,320,093 | A | * | 6/1994 | Raemer .................. | 128/203.12 |
| 5,435,298 | A | * | 7/1995 | Anthony ................ | 128/201.13 |
| 5,836,300 | A | * | 11/1998 | Mault .................... | 128/204.23 |
| 6,042,550 | A | * | 3/2000 | Haryadi et al. ............. | 600/504 |
| 6,095,135 | A | * | 8/2000 | Clawson et al. ....... | 128/201.13 |
| 6,106,480 | A | * | 8/2000 | Gama De Abreu et al. . | 600/529 |
| 6,474,335 | B1 | * | 11/2002 | Lammers ............... | 128/205.12 |
| 6,536,429 | B1 | * | 3/2003 | Pavlov et al. .......... | 128/203.26 |
| 6,550,476 | B1 | * | 4/2003 | Ryder ..................... | 128/201.13 |
| 6,564,799 | B2 | * | 5/2003 | Fukunaga et al. ..... | 128/205.29 |
| 6,588,421 | B1 | * | 7/2003 | Diehl et al. ............ | 128/201.13 |
| 2002/0169385 | A1 | | 11/2002 | Heinonen et al. | |

FOREIGN PATENT DOCUMENTS

| | | |
|---|---|---|
| WO | 98/26710 | 6/1998 |
| WO | 99/25244 | 5/1999 |
| WO | 01/62148 | 8/2001 |

OTHER PUBLICATIONS

"A new method for noninvasive bedside determination of pulmonary blood flow", A. Gedeon et al., Medical & Biological Engineering and Computing, Jul. 1980, pp. 411–418.

"Nunn's Applied Respiratroy Physiology", J. F. Nunn, published by Butterworth1993, pp. 224–225.

"A deep breath method for noninvasive estimation of cardiopulmonary parameters", R. R. Mitchell, International Journal of Clinical Monitoring and Computing 5:53–64, 1988.

* cited by examiner

Primary Examiner—Aaron J. Lewis
(74) Attorney, Agent, or Firm—Andrus, Sceales, Starke & Sawall, LLP

(57) ABSTRACT

Apparatus and method for providing breathing gases to a subject employs an exchanger taking up a quantity of a given component, such as $CO_2$, from expiratory breathing gases passing through the exchanger and thereafter releasing the given component in inspiratory breathing gases subsequently passing through the exchanger. The exchanger may be selectively inserted in a flow path for the breathing gases for this purpose. Or, the breathing gases may be selectively passed through and bypassed around the exchanger. The apparatus and method may be used for non-invasive determination of the functional cardiac output of a patient using the differential form of the Fick equation.

15 Claims, 4 Drawing Sheets

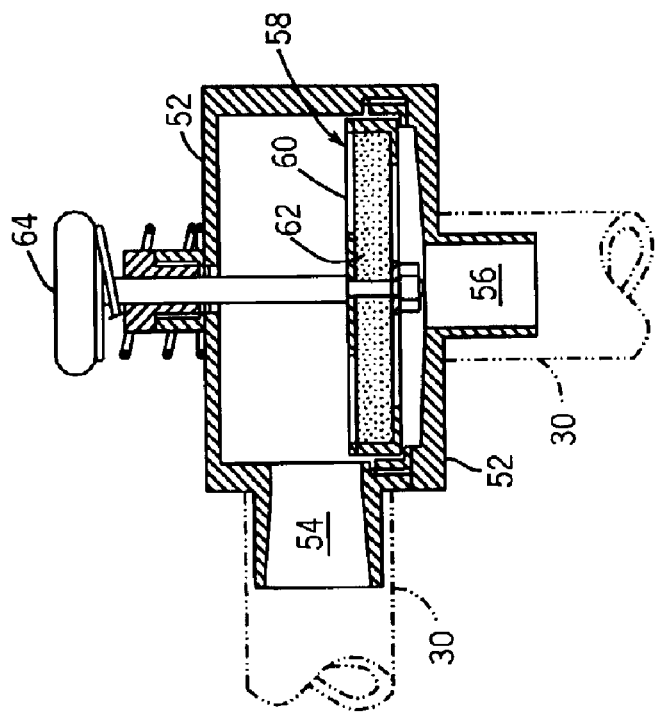
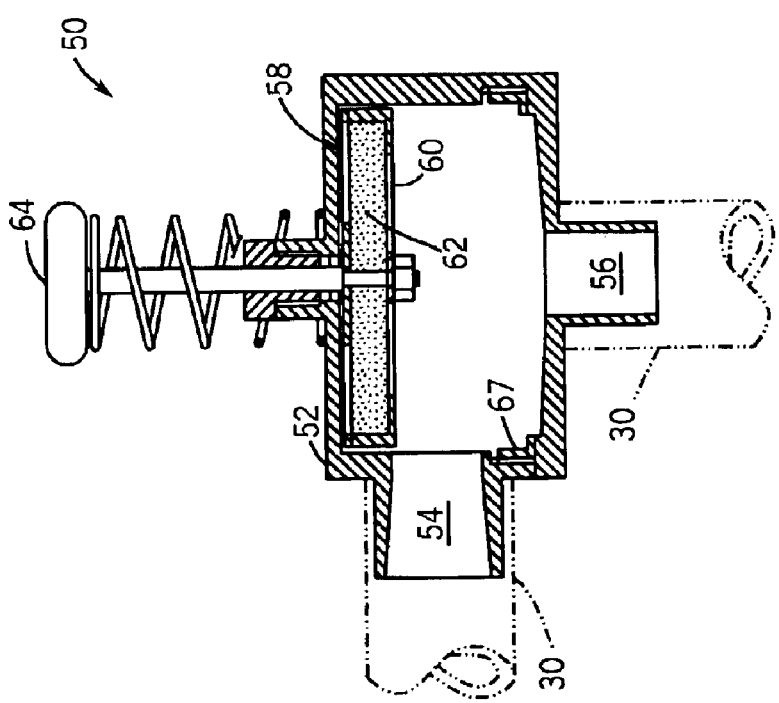

APPARATUS AND METHOD FOR USE IN NON-INVASIVELY DETERMINING CONDITIONS IN THE CIRCULATORY SYSTEM OF A SUBJECT

BACKGROUND OF THE INVENTION

The present invention relates to apparatus and method for use in non-invasively determining a condition of the circulatory system of a subject. More particularly, the present invention is directed to an apparatus and method for non-invasively determining the functional cardiac output of the heart.

The physiological function of the heart is to circulate blood through the circulatory system to the body and lungs. For this purpose, the heart receives blood in arterial chambers during its relaxed or diastolic phase and discharges blood from its ventricle chambers during the contractile or systolic phase. The amount of blood discharged from a ventricle chamber of the heart per unit time is the cardiac output (CO). A typical cardiac output for the heart of a normal adult (at rest) is 5–6 liters per minute.

During circulation through the body, the blood is depleted of oxygen ($O_2$) and is enriched with carbon dioxide ($CO_2$) as a result of the metabolic activity of the body. A major purpose for blood circulation is to take venous blood that has been depleted in $O_2$ and enriched in $CO_2$ as a result of its passage through the tissues of the body and supply it to the lungs. In the alveoli of the lungs, $O_2$ is supplied to the blood from the breathing gases, typically air, and $CO_2$ is discharged into the breathing gases. The oxygenated arterial blood is then supplied to the body tissues. The gas exchange takes place in the capillaries of the lung because of the differences in concentration, or partial pressure, of $O_2$ and $CO_2$ in breathing gases, such as air, and in the venous blood. That is, the blood is low in $O_2$ and high in $CO_2$ whereas air is high in $O_2$ and low in $CO_2$.

A common condition reducing the gas exchange efficiency of the lungs is the presence of shunt perfusion or blood flow in the lungs. A shunt comprises pulmonary blood flow that does not engage in gas exchange with breathing gases, due to blockage or constriction in alveolar gas passages, or for other reasons. This shunt blood flow thus bypasses normal alveoli in which gas exchange is carried out. Upon leaving the lungs, the shunt blood flow mixes with the non-shunt blood flow. The former reduces the oxygen content and increases the $CO_2$ content in the mixed arterial blood supplied to the body tissues.

It will be appreciated that only the non-shunt pulmonary blood flow through the lungs participates in the gas exchange function of the lungs and in oxygenation and $CO_2$ removal in the blood of the subject. The quantity of blood that participates in such pulmonary gas exchange in the lungs is termed functional cardiac output (FCO). For diagnostic or other purposes, it is frequently desirable or essential to know this quantity.

While shunt conditions can occur in the lungs due to blockage brought about by disease, mechanical ventilation, particularly when the respiratory muscles of a subject are relaxed as during anesthesia, can result in an increase in the pulmonary shunt. The breathing gases supplied to the lungs can be enriched with oxygen under such conditions to assist in oxygenation of the blood. However, a sufficient amount of $CO_2$ may not be removed from the blood when the pulmonary shunt is increased, giving rise to potentially adverse consequences to the subject.

The classic technique for determining the functional cardiac output of the heart is through use of the Fick equation $$FCO = \frac{VCO_2}{CvCO_2 - CcCO_2} \qquad (1)$$

where, $VCO_2$ in ml/min. is the amount of CO2 released from the blood in the circulatory system of the subject, $CvCO_2$ is the mixed venous blood $CO_2$ content, for example in ml $CO_2$/ml of blood, and $CcCO_2$ is the end capillary blood $CO_2$ content, i.e. the $CO_2$ content in the blood leaving the ventilated lungs.

The Fick equation states that, knowing the amount of $CO_2$ gas released from the blood in a unit of time (e.g. the rate of gas transfer as a volume/minute) and the concurrent gas transfer occurring per unit of blood (i.e. volume of gas/volume of blood), the blood flow through the lungs (i.e. FCO expressed in volume/minute) can be determined.

If a portion of the pulmonary blood flow of the subject is in shunt, this will decrease the amount of $CO_2$ released from the blood and the computation of Equation (1) provides an indication of the resulting decrease in functional cardiac output. In computing functional cardiac output using the Fick equation, the quantity $VCO_2$ can be determined non-invasively by subtracting the amount of $CO_2$ of the inhaled breathing gases, for example air, from the amount of $CO_2$ of the exhaled breathing gases, taking into account changes in the amount of $CO_2$ stored in the lungs and the deadspace in the breathing organs of the subject, such as the trachea and bronchi. The amount of $CO_2$ stored in the lungs can be computed from the alveolar $CO_2$ gas concentration, as determined from an end tidal breathing gas measurement, and the end expiratory volume $V_{EE}$ of the lungs. The end capillary blood $CO_2$ content ($CcCO_2$) can be determined non-invasively, with a fair degree of accuracy, from a measurement of the concentration of $CO_2$ in the breathing gases exhaled at the end of the expiration of a tidal breathing gas volume, i.e. the end tidal (ET) $CO_2$ level. See also *Respiratory Physiology*, by J. F. Nunn, published 1993 by Butterworths.

The venous blood $CO_2$ content ($CvCO_2$), is often determined invasively. An alternate non-invasive approach for the determination of the $CvCO_2$ can be seen in U.S. Pat. No. 6,042,550 and WO 01/62148. In these approaches, exhaled $CO_2$ enriched breathing gases are rebreathed by the subject in subsequent inhalations. As rebreathing of the exhaled breathings gases continues, breath-by-breath, the end tidal $CO_2$ partial pressure ($P_{ET}CO_2$) increases until the end capillary blood $CO_2$ partial pressure ($P_cCO_2$) is reached. At this point, it is postulated that the end tidal $CO_2$ partial pressure ($P_{ET}CO_2$), the alveolar $CO_2$ partial pressure ($P_ACO_2$), the end capillary blood $CO_2$ partial pressure ($P_cCO_2$), and the venous blood $CO_2$ partial pressure ($P_vCO_2$) are all equal and that this partial pressure can be converted to the venous $CO_2$ content ($C_vCO_2$) for use in the Fick equation.

The need for the determination of the venous blood $CO_2$ content ($C_vCO_2$) is eliminated by the use of a differential form of the Fick equation which arises from the following circumstances. As a subject rebreathes exhaled breathing gases, the end tidal $CO_2$ partial pressure ($P_{ET}CO_2$) and thus the alveolar $CO_2$ partial pressure ($P_ACO_2$) and end capillary $CO_2$ content increases. This reduces the venous blood-alveolar $CO_2$ partial pressure differences and because this is the driving force for $CO_2$ elimination in the lungs, $CO_2$ elimination is also reduced. It has been shown that the ratio of the change in $CO_2$ elimination to the change in the end capillary blood $CO_2$ content is equal to the functional cardiac output. See Gedeon A., et al. Med. Biol. Eng. Comp. 18:411-418 (1980). It is set forth in equation form, as follows:

$$FCO = \frac{VCO_2^N - VCO_2^R}{CcCO_2^R - CcCO_2^N} = \frac{\Delta VCO_2}{\Delta CcCO_2} \qquad (2)$$

In the differential form of the Fick equation, the superscript N indicates values obtained in "normal" breathing conditions. The superscript R indicates values obtained during a short term "reduction" in the $CO_2$ partial pressure difference between that in the alveoli and that in the blood. This results in reduced $CO_2$ transfer in the lungs.

In using the differential form of the Fick equation, a first set of values for $VCO_2$ and $CcCO_2$ are obtained, as in the manner described above, under normal breathing conditions. These are identified by the superscript N. Thereafter, the amount of $CO_2$ in the breathing gases for the subject is increased. This maybe accomplished by a partial re-breathing of exhaled breathing gases. See U.S. Pat. Nos. 5,836,300 or 6,106,480 and published International Patent Appln. WO 98/26710 that employ valve mechanisms, to vary the re-breathed gas volume, for this purpose. Or, this may be accomplished by injecting $CO_2$ into the inhaled breathing gases as described in U.S. Pat. No. 4,608,995. Further possibilities for altering the alveolar $CO_2$ content include varying lung ventilation. This may be accomplished by altering the tidal volume or the respiration rate. Single breath maneuvers such as a deep breath as presented by Mitchell R R in Int J Clin Mon Comp 5:53–64 (1988), inspiratory hold as presented in WO 99/25244, or expiratory hold, may also be used for the purpose.

The $CO_2$ enrichment increases the concentration of $CO_2$ in the alveoli in the lungs and reduces the $CO_2$ partial pressure difference between that of the breathing gases in the lungs and that in the venous blood. As noted above, it is that $CO_2$ partial pressure difference that drives the $CO_2$ gas transfer from venous blood to the breathing gases in the alveoli of the lungs. The reduced $CO_2$ partial pressure difference reduces $CO_2$ gas transfer in the lung and causes an elevation of the $CO_2$ content in the blood downstream of the lung, i.e. in the arterial blood of the subject. In the time interval before the blood with elevated $CO_2$ content circulates through the body and returns to the lungs, the $CO_2$ content of venous blood ($CvCO_2$) entering the lungs can be taken to be the same for both the initial, normal breathing conditions (N) and the subsequent, reduced $CO_2$ partial pressure difference conditions labeled by the superscript R. This similitude permits the factor $CvCO_2$ to be dropped out of the Fick equation when expressed in the differential form as Equation 2 so that the cardiac output is determined by the ratio of the change in released $CO_2$ amounts ($VCO_2$) between the normal (N) and reduced (R) gas exchange conditions to the corresponding change in the end capillary blood $CO_2$ content ($CcCO_2$) in the normal and reduced (R) gas exchange conditions. The need to determine the venous blood $CO_2$ content ($CvCO_2$) from the subject is thus eliminated.

The foregoing approach is also advantageous with ventilated or anesthetized subjects since the alteration of the $CO_2$ content of the breathing gases can be effected by altering the ventilation provided to the subject. In the case of a subject anesthetized with a breathing circuit of the recirculating type, the alteration in $CO_2$ content may be carried out by bypassing the $CO_2$ absorber in the breathing circuit. The $CO_2$ absorber removes $CO_2$ from exhaled breathing gases of the subject thereby allowing the breathing gases to be recirculated to form inspiratory breathing gases for the subject. Bypassing the absorber increases the amount of $CO_2$ in the breathing gases that are recirculated to the subject for inspiration.

While the above described techniques avoid the need to invasively determine venous blood $CO_2$ content, other problems are created. In cases in which a subject is being provided with a fixed volume of breathing gases, an increased re-breathing volume is accompanied by a decreased volume of inspired oxygen. This may produce an undesired reduction in the oxygen content in the blood or require increased oxygen concentrations in the inspired breathing gases, following a cardiac output measurement, to restore oxygen levels in the blood to desired values. Also the tubing required for the large re-breathing volume adds to the size of associated valve systems making them big and bulky when assembled at the very crowded area near the mouth and nose of the subject. Such apparatus also adds to the overall ventilation dead-space volume between the breathing circuit for the subject and the subjects lungs. This increases the amount of ventilation required, adding to the risk of lung distension.

The injection of carbon dioxide into inspired breathing gas overcomes the problems of reduced oxygenation and bulky valve systems, but raises analogous problems. The $CO_2$ is obtained from a gas source and is typically injected using a gas tube. Such a tube is not normally present at the point of care for the subject and adding such a tube, with the accompanying high-pressure regulators and supply conduits, into the already crowded care environment is also undesirable.

BRIEF SUMMARY OF THE INVENTION

An object of the present invention is to provide an improved apparatus and method for carrying out an alteration in the $CO_2$ content of breathing gases inspired by a subject for purposes of non-invasively determining a circulatory system condition, e.g. the functional cardiac output, of a subject.

Another object of the present invention is to provide an apparatus and method that can carry out such alteration without affecting the exchange of other respiratory gases, such as oxygen, in the lung.

Yet another object of the present invention is to provide such apparatus that minimizes disturbance to a patient care environment and minimizes the overall increase in the breathing circuit-lung dead-space volume.

Briefly, in accordance with the improved apparatus and method of the present invention for altering the $CO_2$ content of the breathing gases, and the lung $CO_2$ partial pressure, the breathing gas flow is selectively guided through a $CO_2$ exchanger in a flow path for the breathing gases. The $CO_2$ exchanger selectively takes up $CO_2$ from the expired breathing gases of the subject and releases it to the breathing gases inhaled in a subsequent inspiration. Such an exchanger can be made of a gas porous element, for example, activated charcoal or zeolite, with pore sizes suitable for the adsorption $CO_2$.

The $CO_2$ exchanger can be in a form of a moveable element, that can, with the aid of a transfer mechanism, be moved into and out a flow path of the breathing gases. Alternatively, especially during prolonged artificial ventilation of a subject in intensive care, when the dry inspiration breathing gas is often humidified and warmed with a heat and moisture exchanger (HME), the $CO_2$ exchanger can be connected in parallel with such an HME. Using a control valve, the breathing gas flow can be directed either through the HME, thereby forming a $CO_2$ exchanger bypass channel, or through the $CO_2$ exchanger. With such an arrangement, an increase of the dead space in the breathing gases pathway is avoided. The temporary interruption of the humidification when the breathing gas is directed through the $CO_2$ exchanger is easily tolerated by the subject. To keep the gas exchange conditions unchanged gases other than $CO_2$, the volume of the $CO_2$ exchanger and associated components is advantageously equal to the volume of the by-pass channel containing the HME.

Breathing gas measurements obtained when the breathing gases are not passing through the exchanger and when they are passing through the exchanger may be used to determine the functional cardiac output of the subject using the differential Fick equation, in the manner described above.

Various other features, objects, and advantages of the invention will be made apparent from the following detailed description and the drawings.

BRIEF DESCRIPTION OF THE SEVERAL VIEWS OF THE DRAWING

In the drawing:

FIG. 3a is a detailed cross sectional view of the apparatus according to the present invention showing a moveable $CO_2$ exchanger element in a position in which the breathing gases of the subject bypass the $CO_2$ exchanger element;

FIG. 3b is a similar view showing the $CO_2$ exchanger element transferred to a position in which it is in the breathing gas flow path;

DETAILED DESCRIPTION OF THE INVENTION

The basic principles of the analytical technique in which the apparatus and method of the present invention find use are as follows. For one or more normal (N) breaths of the subject, values are obtained for the amount of $CO_2$ released from the blood ($VCO_2^N$) and for a quantity indicative of the end capillary blood $CO_2$ content, for example $CcCO_2^N$. One or more values for the same quantities are obtained under conditions of reduced (R) gas exchange in the lungs of the subject, to comprise $VCO_2^R$ and $CcCO_2^R$ values. This is accomplished by enriching the inspired breathing gases with $CO_2$. The breathing gases are then, again, returned to the normal condition.

Figure 1:
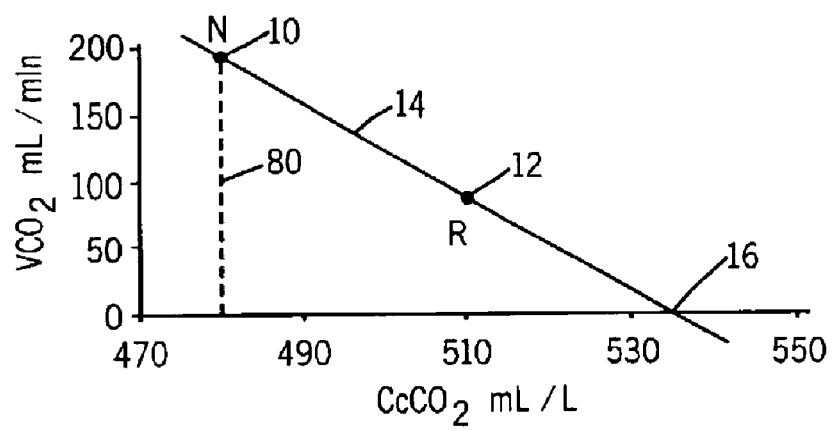
FIG. 1 is a graph showing data obtained from the breathing gases of a subject under normal breathing conditions and under conditions of reduced gas exchange in the lungs of the subject.

The normal (N) breathing values (N) and reduced (R) gas transfer values (R) are used as data points for a regression analysis, such as a linear regression analysis. Graphically, the data points may be plotted on a graph in which the end capillary $CO_2$ blood quantity values, such as $CcCO_2$, are scaled along the abscissa and values for the released amount of $CO_2$ ($VCO_2$) are scaled along the ordinate. Such a graph is shown in FIG. 1. For simplicity only, a single set of N and R data points are shown in FIG. 1 as points 10 and 12, respectively. The regression analysis produces a straight line 14 providing the best fit for the data points. In the simplified example shown in FIG. 1, this is a straight line intersecting the two data points. The downward slope of line 14 makes it clear that the greater the amount of $CO_2$ that is released in the exhalations of the subject, the less will be the end capillary blood $CO_2$ content of the subject.

It will also be appreciated that the slope of line 14 represents the functional cardiac output of the subject as expressed in the differential form of the Fick equation, Equation 2. That is, the difference between the amount of $CO_2$ ($VCO_2$) released under normal (N) conditions and that released under reduced (R) gas transfer conditions shown along the ordinate of FIG. 1 represents the numerator of Equation 2. The corresponding situation exists with respect to the difference in end capillary blood $CO_2$ content ($CcCO_2$) shown on the abscissa of FIG. 2 and forming the denominator of Equation 2. When Equation 2 is presented graphically in the manner shown in FIG. 1, the functional cardiac output thus determined will have a negative sign due to the transposition of the quantities forming the denominator of the equation.

Figure 2:
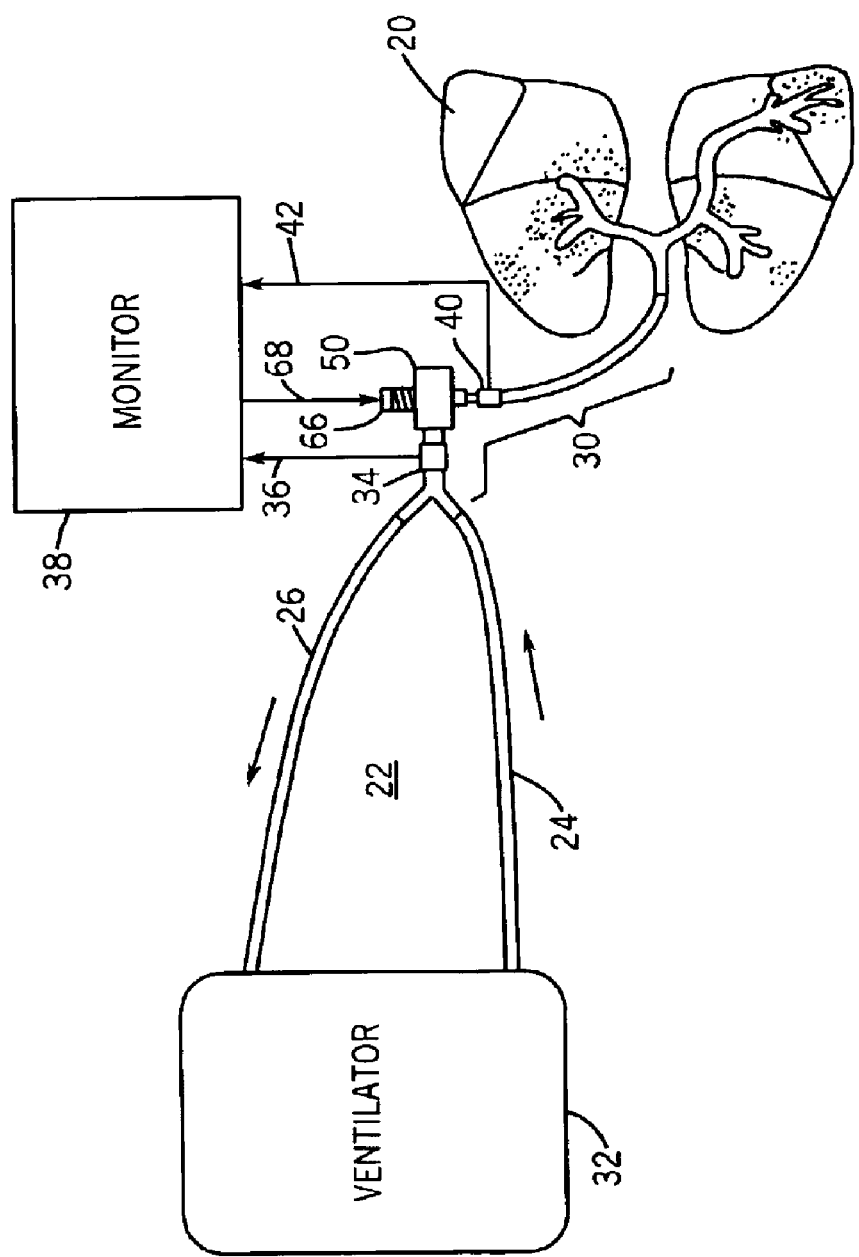
FIG. 2 shows a breathing device using the apparatus of the present invention in order to determine functional cardiac output.

FIG. 2 shows a device suitable for incorporating the apparatus of the present invention and carrying out the method of the present invention. The breathing organs of the subject, including lungs 20 are supplied with breathing gases through breathing circuit 22 of conventional construction. Breathing circuit 22 includes inspiration limb 24 that supplies breathing gases to the subject and expiration limb 26 that receives exhaled gases from the subject. Inspiration limb 24 and expiration limb 26 are connected to two arms of Y-connector 28. A third arm of Y-connector 28 is connected to patient limb 30. Patient limb 30 supplies and receives breathing gases to/from the subject through an endotracheal tube, face mask, or other appliance (not shown).

The other ends of inspiration limb 24 and expiration limb 26 are connected to ventilator 32. Ventilator 32 provides breathing gases in inspiration limb 24 and receives breathing gases from expiration limb 26.

The patient limb accommodates also a flow sensor 34 connected through a signal line 36 to the monitor 38. A flow measuring apparatus suitable for use in breathing circuit 22 is shown in U.S. Pat. No. 5,088,332 to Instrumentarium Corp. of Helsinki, Finland. A hot wire anemometer may also be used for this purpose. The flow sensor may also be placed elsewhere in the circuit than at the location shown in FIG. 2. A $CO_2$ sensor 40 is also located at the patient limb. This sensor can be of mainstream type when the signal line 42 is an electrical one and the active sensor element, typically based on infrared light absorption, is measuring the gas flow in the patient limb. Alternatively, the $CO_2$ sensor 40 may be of sidestream type, when the element in the patient limb is a sampling port and the line 42 is a sampling line conveying a sample gas flow to the infrared analysis within the monitor 38. The $CO_2$ sensor is used to determine the end-tidal $CO_2$ concentration and, together with the flow signal from flow sensor 34, is used to determine the $CO_2$ elimination from the lungs by integrating the product of instantaneous flow and the corresponding $CO_2$ concentration.

The output of sensors 34 and 40 are provided in signal lines 36 and 42 to monitor 38 in which the integration of flow rates to obtain volumes, filtering, or other signal processing is carried out to produce values for the sensed quantities.

Sensors 34 and 40 and monitor 38 measure gas flows, expired $CO_2$ concentrations, and end tidal $CO_2$ gas concentrations. Measured expired $CO_2$ concentrations and gas flows can be used to determine the amount of $CO_2$ ($VCO_2$) released from the blood. The end tidal $CO_2$ concentration is used to determine quantities indicative of the $CO_2$ content of the blood, such as $CcCO_2$, as described above.

As shown in FIG. 2, the $CO_2$ exchanger apparatus 50 of the present invention is located in the patient limb 30. One embodiment of the exchanger apparatus is shown in FIGS. 3a and 3b. $CO_2$ exchanger apparatus 50 has housing 52 with ports 54 and 56 for connecting the $CO_2$ exchanger apparatus in patient limb 30, as shown in FIG. 2. As shown in FIG. 2, $CO_2$ exchanger apparatus 50 is connected in patient limb 30 upstream of $CO_2$ sensor 40. That is, $CO_2$ sensor 40 is positioned between $CO_2$ exchanger apparatus 50 and the subject, i.e. subject's lungs 20. Housing 52 of $CO_2$ exchanger apparatus 50 includes a moveable element 58 containing a substance capable of taking up a quantity of $CO_2$ from expiration breathing gases passing through the element and thereafter releasing the taken up quantity of $CO_2$ to inspired breathing gases subsequently passing through the element. For this purpose and by way of example, element 58 may comprise a porous housing 60 containing activated charcoal rods. Such a material adsorbs the $CO_2$ from the high $CO_2$ partial pressure expiration breathing gases, and due to the weakness of the bonding of the $CO_2$ to the absorption material, thereafter releases or relinquishes the $CO_2$ to the low $CO_2$ partial pressure inspiration breathing gases. The two-way taking up and releasing action of the $CO_2$ exchanger of the present invention distinguishes it from a $CO_2$ absorber conventionally found in recirculating breathing circuits. The function of a $CO_2$ absorber is to permanently remove $CO_2$ from the breathing gases of a patient. The activated charcoal rods may, for example, be 1 mm in diameter and 1–5 mm in length. A typical volume of material for taking up $CO_2$ and releasing a sufficient quantity to adequately increase the alveolar $CO_2$ partial pressure is 10–30 ml, depending the exact geometry of apparatus 50 and element 58. For an apparatus suitable for pediatric patients the volume of $CO_2$ absorption/release material may be smaller. Other materials, such as zeolite with pore sizes suitable for the adsorption of $CO_2$ may also be used.

Element 58 may be moved from a position which is shown as an upper position in FIG. 3a, to a lower position shown in FIG. 3b. In the simplest embodiment of the invention, a manual actuator 64 may be employed as a transfer mechanism for this purpose. In a typical, practical embodiment of the present invention shown in FIG. 2, manual actuator 64 is replaced with an electrical solenoid or linear motor 66 operable by a signal in line 68 from monitor 38. It would also be possible to provide a pneumatic actuator in apparatus 50.

With element 58 in the raised, upper position shown in FIG. 3a, breathing gases to/from the patient proceed directly between ports 54 and 56 of housing 52 of apparatus 50. With element 58 in the lowered position, shown in FIG. 3b, breathing gases passing between ports 54 and 56 pass through element 58 and the gas take up/release substance 62. A seal 67 may be provided in the lower portions of housing 52 to accommodate element 58 when it is in the lowered position.

The method for carrying out the method of the present invention is as follows. The method is described as in an instance using air for the breathing gases. Respiration may be either spontaneous on the part of the subject or assisted by the ventilation apparatus shown in FIG. 2.

Element 58 of apparatus 50 is placed in the upper position shown in FIG. 3a. The subject breathes, or is ventilated, with breathing gases such as air. The normal (N) breathing action of the subject is allowed to stabilize. This may, for example, require a minimum of five breaths or a half a minute to a minute of time. The amount of $CO_2$ released from the blood in the lungs of the subject and the $CO_2$ concentration in the breathing gases are then measured, for at least one breath, or preferably for each of a plurality of breaths, of the subject using sensors 34 and 40. Typically, the $CO_2$ concentration is measured as the end tidal $CO_2$ concentration ($P_{ET}CO_2^N$). One or more values of $VCO_2$ (N) are determined. In this exemplary description, the quantity used to describe the end capillary blood $CO_2$ condition is the $CO_2$ content ($CcCO_2$). The measured end tidal $CO_2$ concentrations are thus used to determine $CcCO_2$ and one or more $CcCO_2$ N values are obtained from the end tidal $CO_2$ levels for the breaths.

Thereafter, the $CO_2$ content of the breathing gases inhaled by the subject is increased to increase the $CO_2$ concentration in the lungs of the subject and to reduce $CO_2$ gas transfer, i.e. (R) breathing conditions. Using the apparatus shown in FIG. 3a, this may be accomplished by lowering element 58 to place the element in the breathing gas flow path between ports 54 and 56, as shown in FIG. 3b.

Figure 4:
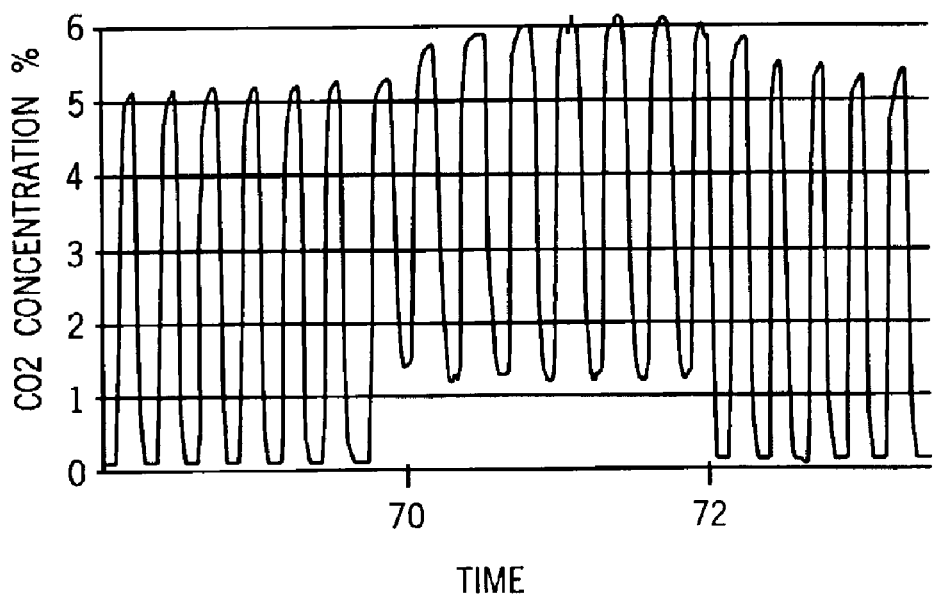
FIG. 4 is a graph of the breathing gas $CO_2$ concentration when the breathing gas is passed through the $CO_2$ exchanger element and when it by-passes the exchanger element.

The end tidal $CO_2$ levels are examined as the subject breathe under these conditions. FIG. 4 shows a read out of the $CO_2$ levels of the breathing gas passing $CO_2$ sensor 40 downstream of apparatus 50. Prior to time 70, element 58 in apparatus 50 is in the raised position so that the breathing action of the subject is in the normal (N) one described above. For each breath, the $CO_2$ level starts at essentially zero during inhalation and rises to about 5% in the exhaled breathing gases.

At time 70, element 58 is lowered into the breathing gas passage between parts 54 and 56. Element 58 commences its $CO_2$ taking up and releasing action. This causes the $CO_2$ content of the inhaled breathing gases to rise to over 1% and the $CO_2$ content of the exhaled breathing gases to increase to about, or over, 6%, as shown in FIG. 4. The result is an increase in the inspired $CO_2$ content of about 1.0% which is considered optimal in carrying out the determination of functional cardiac output.

When the end tidal $CO_2$ levels no longer change, this indicates that the alveolar $CO_2$ concentration in the lungs is constant, which means that $CO_2$ storage in the lungs has been accommodated. The measurement of the amount of gas released from the lungs of the subject and $CO_2$ concentrations of the breathing gases, i.e. end tidal $CO_2$ concentration, is then commenced. After measurements are taken, the enrichment of $CO_2$ in the inhaled breathing gases may thereafter be terminated by raising the $CO_2$ take up/release element 58 to the upper position shown in FIG. 3a at time 72.

The exact amount and duration of the $CO_2$ enrichment will depend on numerous physical and physiological factors of the patient and on the data needed to accurately determine functional cardiac output. For a typical adult, $CO_2$ enrichment would last about 6 or 10 breaths.

The amount of end-tidal $CO_2$ increase is governed by somewhat conflicting considerations. The larger the increment, the larger will be the alveolar $CO_2$ concentration in the lungs and the end capillary blood $CO_2$ content ($CcCO_2$). This will place the R data point 12 farther from the abscissa of FIG. 1 and improve the accuracy of the FCO determination. On the other hand, the larger the $CO_2$ increase is, the less $CO_2$ gas exchange occurs in the lungs of the subject resulting in higher $CO_2$ blood levels that require a longer time to return to normal levels. The optimum of $CO_2$ increase a combination of these factors and need be no greater than that required to achieve the desired results.

The amount of $CO_2$ released from the blood of the subject ($VCO_2^R$) is determined by subtracting the amount of $CO_2$ in the enriched, inhaled breathing gases from the $CO_2$ amount measured in the exhaled breathing gases. The measured end tidal $CO_2$ levels are used to determine the end capillary blood $CO_2$ content $CcCO_2^R$. These determinations are carried out from measurements obtained within the circulation period of the blood in the body of the subject following the switching of actuator 64, 66 to transfer the $CO_2$ take up/release element 58 into the breathing gas flow path. This is a period of approximately 20 seconds to one minute. In this period, the venous blood $CO_2$ content ($CvCO_2$) remains constant since it has not yet returned to the lungs to undergo gas exchange.

If desired, an administration of increased $CO_2$ in the inhaled breathing gases to the subject can be repeated after an appropriate interval during which $CO_2$ levels in the blood return to normal.

A regression analysis, such as a linear regression analysis, is then performed using the normal (N) values obtained from the initial breaths of the patient prior to time 70 in FIG. 40 and the reduced (R) gas transfer values obtained following the increase in the $CO_2$ content of the inhaled breathing gases, i.e. after time 70. It will be appreciated that the data used to perform the regression analysis can include many normal (N) values obtained from the plurality of normal breaths taken by the patient. There will be a smaller number of R values due to the time limitation set by the blood recirculation.

As noted above, the slope of line 14 produced by the regression analysis is the negate of the functional cardiac output (FCO) of the patient.

Figure 5:
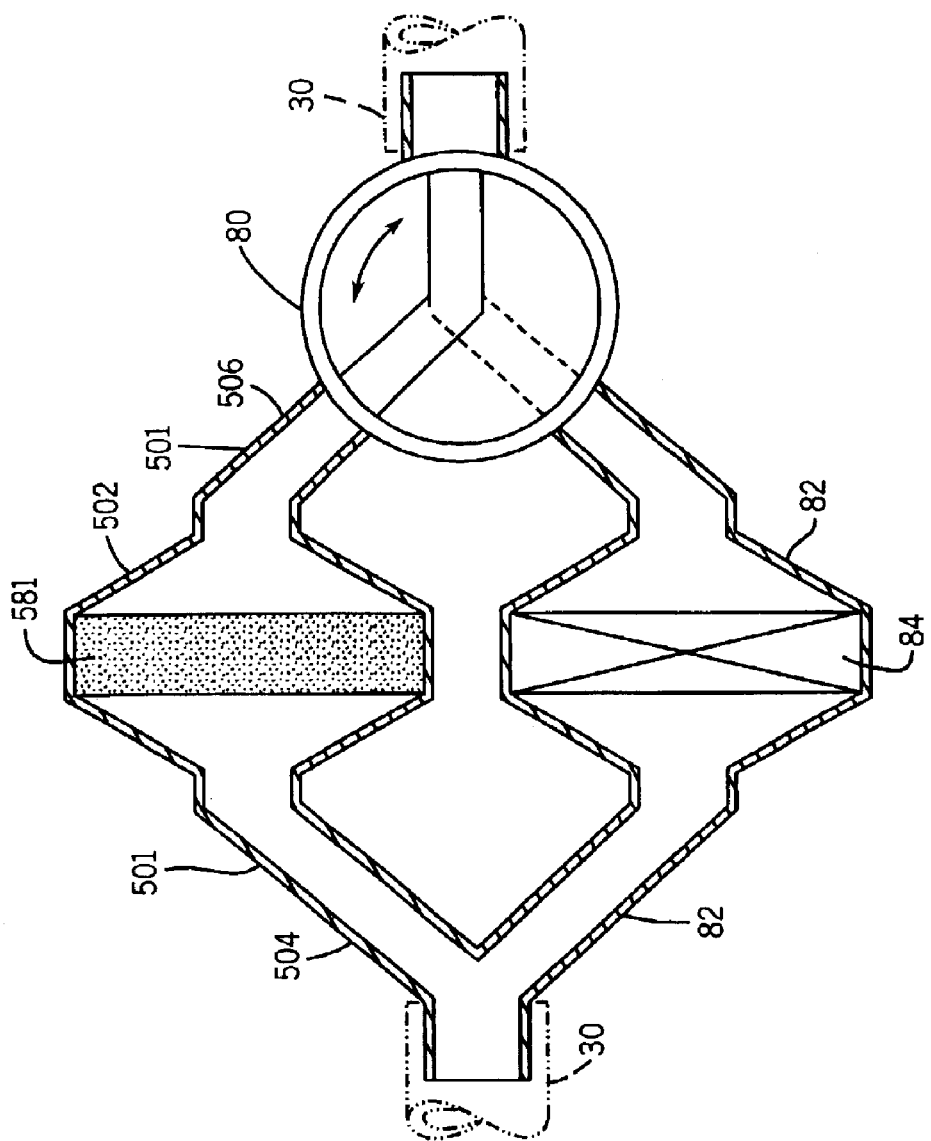
FIG. 5 is an alternative embodiment of the $CO_2$ exchanger apparatus of the present invention connected in parallel to a heat and moisture exchanger.

FIG. 5 presents an alternate embodiment in which the $CO_2$ take the $CO_2$ up/release element is positioned in parallel with a heat and moisture exchanger (HME). Specifically, apparatus 501 contains $CO_2$ take up/release element 581. Element 581 may be similar in construction to element 58 except that it is not moveable in the housing 502 of apparatus 501. Housing 502 contains ports 504 and 506. Part 504 may be connected in patient limb 30. Part 506 is connected to valve 80.

Heat and moisture exchanger 82 is connected in parallel with apparatus 501 between patient limb 30 and valve 80. Valve 80 is also connected to patient limb 30. Heat and moisture exchanger 82 may be of conventional construction and includes a component 84, schematically shown in FIG. 5, for carrying out its intended purpose.

By the appropriate operation of valve 80, the breathing gases of the subject can bypass apparatus 501 and pass through heat and moisture exchanger 82, as prior to time 70 and subsequent to time 72, or pass through apparatus 501, as between timer 70 and 72.

It is preferable that the volumes of the apparatus 501 and its associated flow paths and the volume of heat and moisture exchanger 82 and its associated flow paths be made essentially equal to avoid changes in the gas exchange of gases other than $CO_2$. An adult heat and moisture exchanger is typically 40 ml by volume, and for pediatric patients the volume may be 15 ml.

It is recognized that other equivalents, alternatives, and modifications aside from those expressly stated, are possible and within the scope of the appended claims.

What is claimed is:

1. Apparatus for altering the amount of $CO_2$ in breathing gases provided to a subject, the subject breathing in respiratory cycles each having an inspiratory phase in which inspiratory breathing gases are provided to the subject and an expiratory phase in which the subject exhales expiratory breathing gases, $CO_2$ being present in the expiratory breathing gases of the subject, said apparatus comprising:
   a conduit means having a flow path for providing inspiratory breathing gases to the subject during the inspiratory phases of the respiratory cycles and receiving expiratory breathing gases from the subject during the expiratory phases of the respiratory cycles;
   a gas component exchanger for taking up a quantity of $CO_2$ from gas passing through said exchanger and releasing $CO_2$ in gas passing through said exchanger; and
   means for selectively passing inspiration and expiration breathing gases in said conduit through said exchanger;
   the exchanger taking up $CO_2$ from the expiratory breathing gases in an expiratory phase and thereafter releasing $CO_2$ into the inspiratory breathing gases in an inspiratory phase to raise the concentration of $CO_2$ in the inspiration breathing gases provided to the subject.

2. The apparatus of claim 1 wherein said means for selectively passing inspiratory and expiratory breathing gases through said exchanger comprises means for selectively inserting said exchanger in said flow path of said conduit means.

3. The apparatus of claim 1 wherein said means for selectively passing inspiratory and expiratory breathing gases through said exchanger comprises means for selectively passing the breathing gases through said exchanger or diverting the breathing gases from said exchanger.

4. The apparatus of claim 3 wherein said means for passing or diverting the breathing gases includes an alternative flow path for the breathing gases containing a gas treatment device.

5. The apparatus of claim 4 wherein said gas treatment device comprises a heat and moisture exchanger.

6. The apparatus of claim 4 wherein the volume of said flow path and exchanger and the volume of said alternative flow path and gas treatment device are substantially the same.

7. The apparatus of claim 3 further including valve means for selectively passing or diverting the breathing gases.

8. The apparatus of claim 1 wherein said exchanger includes activated charcoal for taking up and releasing $CO_2$ in breathing gases passing through the exchanger.

9. The apparatus of claim 1 wherein said exchanger includes zeolite for taking up and releasing $CO_2$ in breathing gases passing through the exchanger.

10. The apparatus of claim 1 further including a ventilator coupled to said conduit means for supplying inspiratory gases to the subject and receiving expiratory gases from the subject.

11. The apparatus of claim 10 further including a flow meter for measuring the flow of breathing gases.

12. The apparatus of claim 10 further including a $CO_2$ measuring means between said exchanger and the subject.

13. A method for altering the amount of $CO_2$ in breathing gases provided to a subject, the subject breathing in respiratory cycles each having an inspiration phase in which inspiratory breathing gases are provided to a subject and an expiration phase in which the subject exhales expiratory breathing gases, $CO_2$ being present in the expiratory breathing gases of the subject, said method comprising the steps of:

passing expiratory breathing gases of the subject along a flow path;

taking up a quantity of $CO_2$ from expiratory breathing gases passing in the flow path; and thereafter releasing $CO_2$ taken up into the inspiratory breathing gases to raise the concentration of $CO_2$ in the inspiratory breathing gases for the subject.

14. The method of claim 13 further including the step of selectively inserting an exchanger into the flow path for the breathing gases, the exchanger taking up a quantity of $CO_2$ from expiratory breathing gases in the flow path and releasing $CO_2$ in inspiratory breathing gases in the flow path.

15. The method of claim 13 further defined as including the step of selectively passing breathing gases through an exchanger or bypassing the breathing gases around the exchanger, the exchanger taking up a quantity of $CO_2$ from expiratory breathing gases passing through the exchanger and releasing $CO_2$ in inspiratory breathing gases passing through the exchanger.

* * * * *